(12) United States Patent
Darty

(10) Patent No.: US 7,095,323 B2
(45) Date of Patent: Aug. 22, 2006

(54) HAZARDOUS MATERIAL MAIL COLLECTION POINT-OF-USE

(75) Inventor: Harry Darty, St. Charles, MD (US)

(73) Assignee: The United States Postal Service, Washington, DC (US)

( * ) Notice: Subject to any disclaimer, the term of this patent is extended or adjusted under 35 U.S.C. 154(b) by 0 days.

(21) Appl. No.: 10/632,466

(22) Filed: Aug. 1, 2003

(65) Prior Publication Data

US 2004/0080414 A1    Apr. 29, 2004

Related U.S. Application Data

(60) Provisional application No. 60/420,980, filed on Oct. 24, 2002.

(51) Int. Cl.
*G08B 13/14* (2006.01)
(52) U.S. Cl. .......................... 340/569; 232/17
(58) Field of Classification Search ................ 340/569, 340/570, 632, 613, 665, 666; 73/23.2, 23.34, 73/866; 232/17, 34, 35, 38, 39
See application file for complete search history.

(56) References Cited

U.S. PATENT DOCUMENTS

| | | | | |
|---|---|---|---|---|
| 2,705,593 A | * | 4/1955 | Haskins | 232/21 |
| 4,363,438 A | * | 12/1982 | Connor | 232/30 |
| 5,023,595 A | * | 6/1991 | Bennett | 340/569 |
| 6,592,026 B1 | * | 7/2003 | Vilardi | 232/17 |
| 6,613,571 B1 | * | 9/2003 | Cordery et al. | 436/48 |
| 6,742,703 B1 | * | 6/2004 | Esakov et al. | 232/45 |
| 6,772,939 B1 | * | 8/2004 | Simpson | 232/38 |
| 6,779,714 B1 | * | 8/2004 | Webb | 232/17 |
| 6,789,727 B1 | * | 9/2004 | Felice et al. | 232/44 |
| 6,792,795 B1 | * | 9/2004 | Jones et al. | 73/37 |

\* cited by examiner

*Primary Examiner*—John Tweel, Jr.
(74) *Attorney, Agent, or Firm*—Finnegan, Henderson, Farabow, Garrett & Dunner LLP

(57) ABSTRACT

A mail collection point-of-use for and method of preventing detected hazardous materials within a mail collection point-of-use from contaminating components of subsequent mail delivery system processes. The mail collection point-of-use comprises a mail drop unit having an opening for receiving customer-deposited mail, a mail receptacle for accumulating received mail, an enclosure coupled to the mail drop unit and containing the mail receptacle and having a door that seals an opening large enough to permit removal of the mail receptacle, a detector inside the enclosure, which generates a detection signal upon detection of airborne hazardous material, and an indicator outside the enclosure for indicating the detection of hazardous material. By indicating the detection of hazardous materials within the mail collection point-of-use before removing the mail receptacle and its contaminated mail, the further spread of the hazardous materials in a mail delivery system may be prevented.

51 Claims, 10 Drawing Sheets

HAZARDOUS MATERIAL MAIL COLLECTION POINT-OF-USE

CROSS REFERENCE TO RELATED APPLICATION

Priority under 35 U.S.C. § 119 is claimed based on U.S. Provisional Application No. 60/420,980, filed on Oct. 24, 2002 the disclosure of which is expressly incorporated herein by reference.

BACKGROUND OF THE INVENTION

1. Technical Field

Embodiments disclosed herein relate to a mail collection point-of-use for reducing the spread of hazardous materials deposited in a mail collection point-of-use to processing equipment in a mail delivery system. In particular, they relate to a mail receptacle which reduces the force of impact experienced by deposited mail, and a mail collection point-of-use which provides an indication of the detection of hazardous materials within it, prior to the removal from the point-of-use of a mail receptacle and its contaminated mail.

2. Description of Related Art

Standard postal points-of-use include the familiar curbside mail collection boxes. They also include the PS 1814 face plate drop unit and 1577 letter drop units in the wall of a lobby of a post office or other building. Points-of-use installed in the wall have corresponding mail receptacles on the opposite side of the wall in a workroom, where the process of mail delivery begins with sortation. A curbside mail collection point-of-use has a mail receptacle within it.

Mail deposited into a postal point-of-use slides and falls from the point of deposit to a landing place, which, in an empty mail receptacle, is the bottom of the mail receptacle. The bottom of the mail receptacle is approximately a meter below the point of deposit. The force of impact with which the mail hits the bottom of the mail receptacle can cause any powdery substance within the mail to escape through openings or porous surfaces into the air. Moreover, as additional mail is deposited on top of the deposited contaminated mail, the contaminated mail becomes compressed, which can force more powdery hazardous material into the air.

In mail receptacles accumulating mail from building lobbies, the mail receptacle has an open top. Thus the air in and near the mail receptacle is not isolated from the rest of the work area containing the mail receptacle. With all types of mail collection points-of-use, a mail handling employee regularly checks to see when the mail receptacle is full. The employee removes the full mail receptacle and places an empty one in its place to accumulate newly deposited mail by customers. The full mail receptacle is taken to the next mail delivery processing equipment. During that subsequent mail processing step of sorting, the pieces of mail are compressed further, enabling any powdery hazardous material contained in the mail to escape the mail through openings or porous surfaces and contaminate the surrounding air and equipment. Contamination of the air and equipment places mail handling employees at risk of exposure to hazardous materials. There is a need to prevent contamination of the air in the work area and the spread of hazardous materials to further mail processing equipment.

Events of 2001 involving anthrax pointed out the need for early detection of hazardous materials in mail or otherwise placed in the mail delivery system for health and successful investigation of the perpetrators, and preferably prior to the mail reaching automated equipment which spread the anthrax within the postal service work areas.

SUMMARY

As embodied and broadly described herein, an embodiment consistent with the invention is a mail collection point-of-use comprising a mail drop unit having an opening for receiving customer-deposited mail and an enclosure coupled to the mail drop unit. The enclosure has an opening and a door sealing the opening when the door is closed. The mail collection point-of-use also comprises a mail receptacle inside the enclosure for accumulating received customer-deposited mail. The receptacle and the enclosure's opening are sized to permit removal of the receptacle from the enclosure through the opening. A detector positioned inside the enclosure generates a detection signal upon detection of airborne hazardous material. The mail collection point-of-use also has an indicator positioned outside the enclosure, which is coupled to the detector and generates an indication upon receipt of the detection signal.

Another embodiment consistent with the invention is a method of preventing detected hazardous materials within a mail collection point-of-use from contaminating components of subsequent mail delivery system processes. The method comprises receiving customer-deposited mail through an opening in a mail drop unit, accumulating received customer-deposited mail in a mail receptacle contained in an enclosure, and examining air within the enclosure for airborne hazardous material. If hazardous material is detected, the method includes generating a detection signal and indicating the detection of hazardous material.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments consistent with the invention and together with the description, serve to explain the principles of the invention. In the drawings.

DESCRIPTION OF EMBODIMENTS

Reference will now be made in detail to the exemplary embodiments consistent with the invention, examples of which are illustrated in the accompanying drawings. Wherever possible, the same reference numbers will be used throughout the drawings to refer to the same or like parts.

Figure 1:
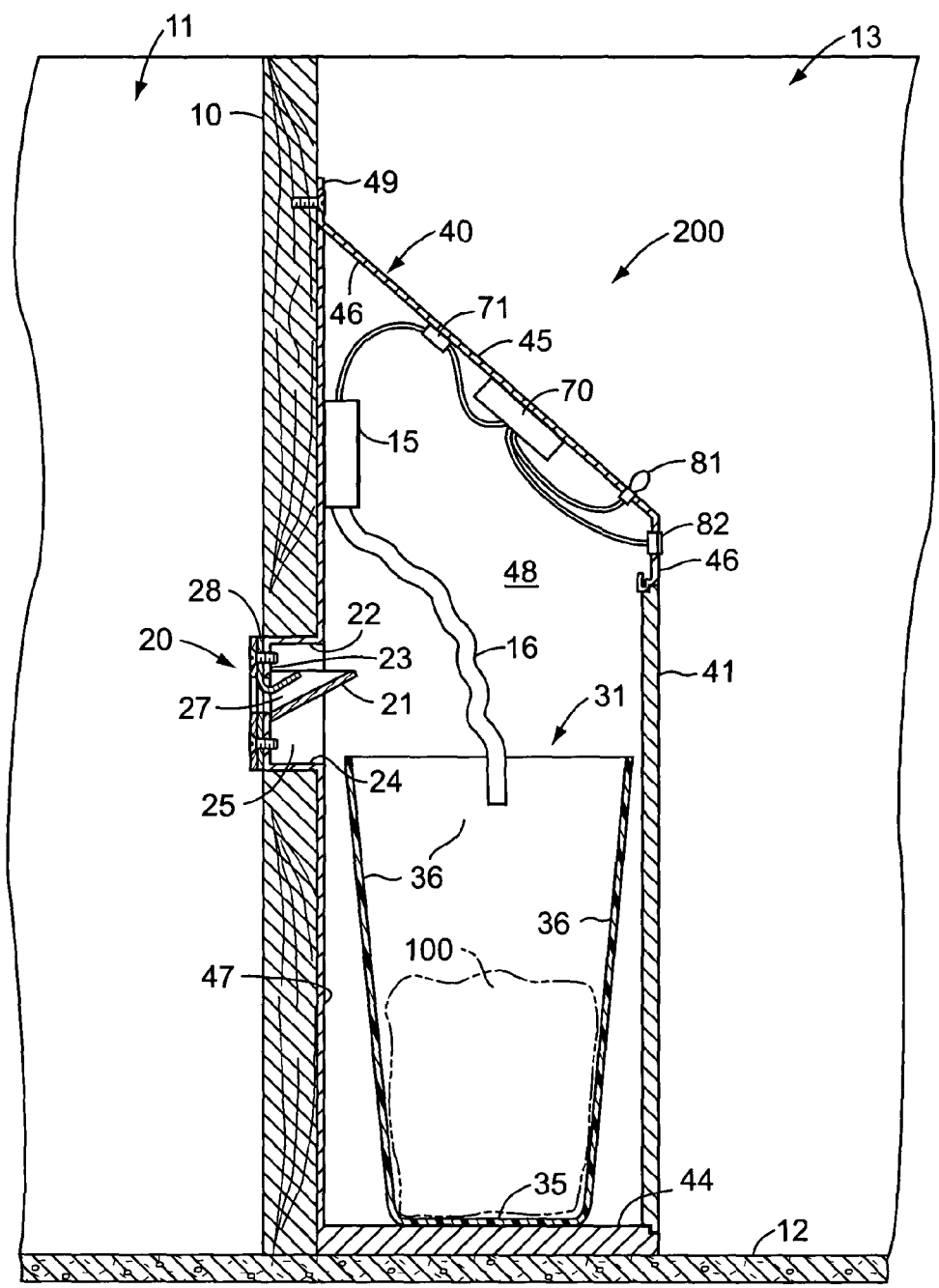
FIG. 1 is a section view of a mail collection point-of-use consistent with the invention taken along line 1—1 of FIG. 2.
Figure 2:
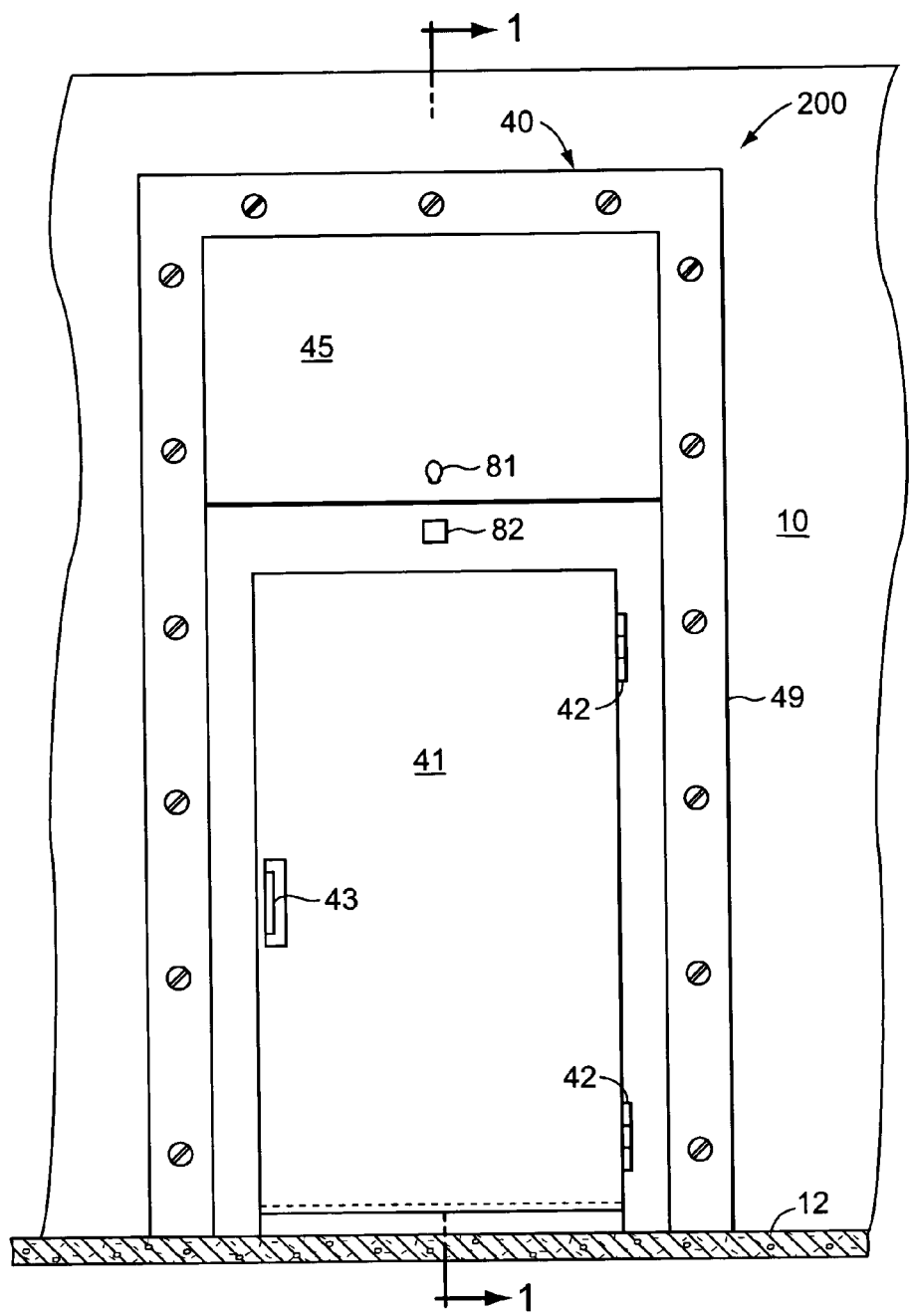
FIG. 2 is a rear view of the mail collection point-of-use of FIG. 1.

As shown in FIGS. 1 and 2, a mail collection point-of-use 200 includes a mail drop unit 20 with a front wall 23 and an opening 27 for receiving customer-deposited mail from a customer accessible area 11, for instance, the public lobby of a United States Post Office or other building. Opening 27 is of an appropriate size and shape to accommodate commonly deposited mail or bundles of mail. Mounted by screws onto front wall 23 in FIG. 1 is a face plate drop unit 28, preferably of a PS 1814 series type, (see FIG. 9), which defines opening 27.

Mail drop unit 20 has a top wall 22, side walls 25, and a bottom wall 24 that match in size and shape the surrounding surfaces of a wall 10, which separates customer-accessible area 11 from a non-customer-accessible work area 13. As illustrated in FIG. 1, a chute 21, is provided for guiding received mail from opening 27 to a rigid, constant-volume container 31 form of a mail receptacle.

As illustrated, container 31 has a bottom wall 35, four side walls 36 that form internal angles greater than ninety degrees with bottom wall 35, and an open top. Container 31 may have any appropriate shape, however. The perimeter of the top of container 31 is positioned to receive deposited mail. Container 31 is shown in FIG. 1 as partially filled with accumulated mail 100.

An enclosure 40 surrounds container 31. Enclosure 40 may be made of any material that does not allow air containing hazardous materials to pass. Enclosure 40 has a bottom wall 44, top wall 45, back wall 46, front wall 47, and two side walls 48. Front wall 47 is connected to side walls 25, top wall 22, and bottom wall 24 of mail drop unit 20. As seen best in FIG. 2, back wall 46 has a sealed door 41 (preferably hermetically sealed) having two hinges 42 and a handle 43. Door 41 is not required to be on back wall 46, but could be on either side wall 48 (FIG. 1) or a combination of back wall 46 and a side wall 48, or even top wall 45. When closed, door 41 hermetically seals an opening sized to permit removal of container 31 (FIG. 1) when full of accumulated mail 100. Enclosure 40 also has a flange 49 that is both secured and sealed to wall 10 and or a floor 12 of work area 13 when attached with flat head slotted wood screws. Alternatively, enclosure 40 could be attached to wall 10 or floor 12 by other appropriate means.

As illustrated in FIG. 1, enclosure 40 contains a detector 70. Detector 70 examines air within mail collection point-of-use 200 for the presence of hazardous material and generates a detection signal upon detection of airborne hazardous material. Detector 70 is attached on top wall 45 of enclosure 40. Enclosure 40 also houses an intermittently activated vacuum fan 15 for increasing the rate at which any airborne hazardous material travels to detector 70. Fan 15 may suck air from container 31, preferably through a flexible duct or tube, such as flexible duct 16, and direct air to detector 70. As illustrated in FIG. 1, fan 15 has a switch, such as an AC/DC control switch circuit 71, wired to detector 70. Control switch circuit 71 may be selectively and automatically opened upon detecting hazardous material to deactivate fan 15. Other appropriate means may be used for increasing the rate at which hazardous material reaches detector 70.

Mail collection point-of-use 200 also includes indicators 81 and 82 coupled to detector 70 and which generates an indication upon receipt of the detection signal. Indicators are preferably sources of visible light but could include broadcast public address system voice messages announcing the presence of hazardous material; scrolling messages on display boards; or audio indicators generating sound, either at a constant value or varied in a pattern once the detector has detected the presence of hazardous materials. Sources of visible light may include LEDs; liquid crystal displays; an incandescent, fluorescent, or neon lights. Audio indicators may include buzzers, horns, sirens, or chimes. Text indicators on enclosure 40 may be used in conjunction with the visual or audio indicators to explain the significance of indication.

As illustrated in FIGS. 1 and 2, indicator 81 is an incandescent bulb for generating visible light and indicator 82 is a buzzer for generating sound upon receipt of the detection signal from detector 70. Bulb 81 and buzzer 82 are mounted on the outside surface of enclosure 40. Detector 70 may be hard-wired to buzzer 82 and bulb 81 or coupled by other appropriate means.

When detector 70 detects hazardous material, it activates buzzer 82 and bulb 81 and deactivates fan 15. A mail handling employee seeing the light from light bulb 81 and or hearing the sound from buzzer 82 is trained to realize that hazardous material has been detected within enclosure 40 and can notify a person with authority to safely handle the hazardous material. An investigation can then be conducted, rather than exposing personnel to the hazardous material when they open door 41 to check on the level of accumulated mail 100 in container 31 and remove container 31 and its contaminated mail. A part of that investigation may include removing mail collection point-of-use 200 to a safe location before opening door 41 to remove container 31 and its contaminated mail. Hazardous material detected within enclosure 40 therefore is not spread to processing equipment in a mail delivery system, such as sortation equipment.

In other embodiments consistent with the invention, as illustrated in FIGS. 3–6, mail collection point-of-use 200 may include a lower positioning structure 59A (FIGS. 3–4) and 59B (FIGS. 5–6) for establishing the bottom of the mail receptacle at an initial position below the top of the mail receptacle and for lowering the bottom of the mail receptacle as a function of the weight of the accumulated mail, thereby reducing the distance the deposited mail falls into an empty mail receptacle and the force with which it lands. The reduced falling distance and landing force reduces the amount of any powdery hazardous material contained in deposited mail that is dispersed through openings and porous surfaces in the mail.

Figure 3:
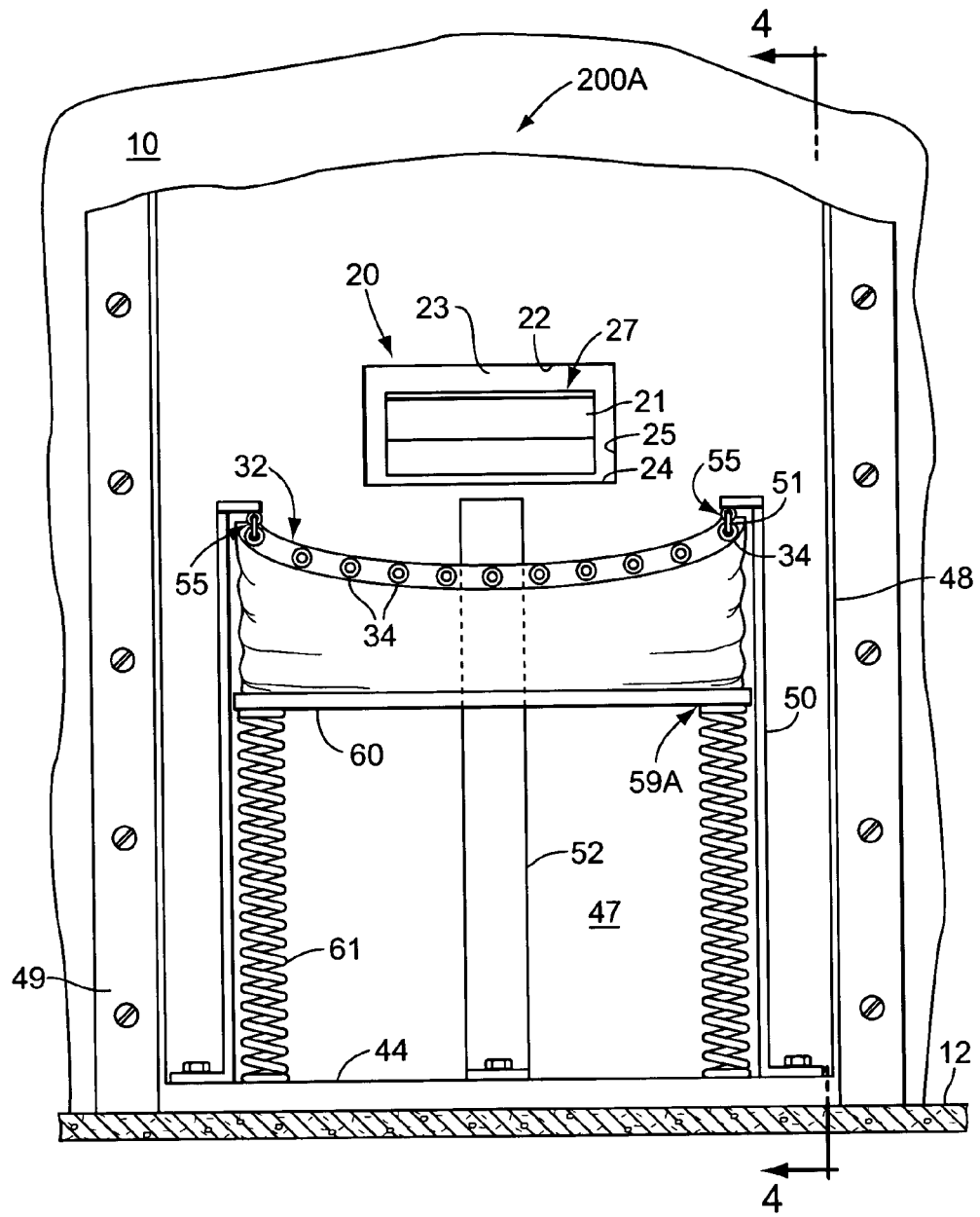
FIG. 3 is a partial rear view of a mail collection point-of-use consistent with the invention having an empty sack and two parallel brackets with hooks engaging grommets in the sack and four springs elevating a platform supporting the bottom of the sack.
Figure 4:
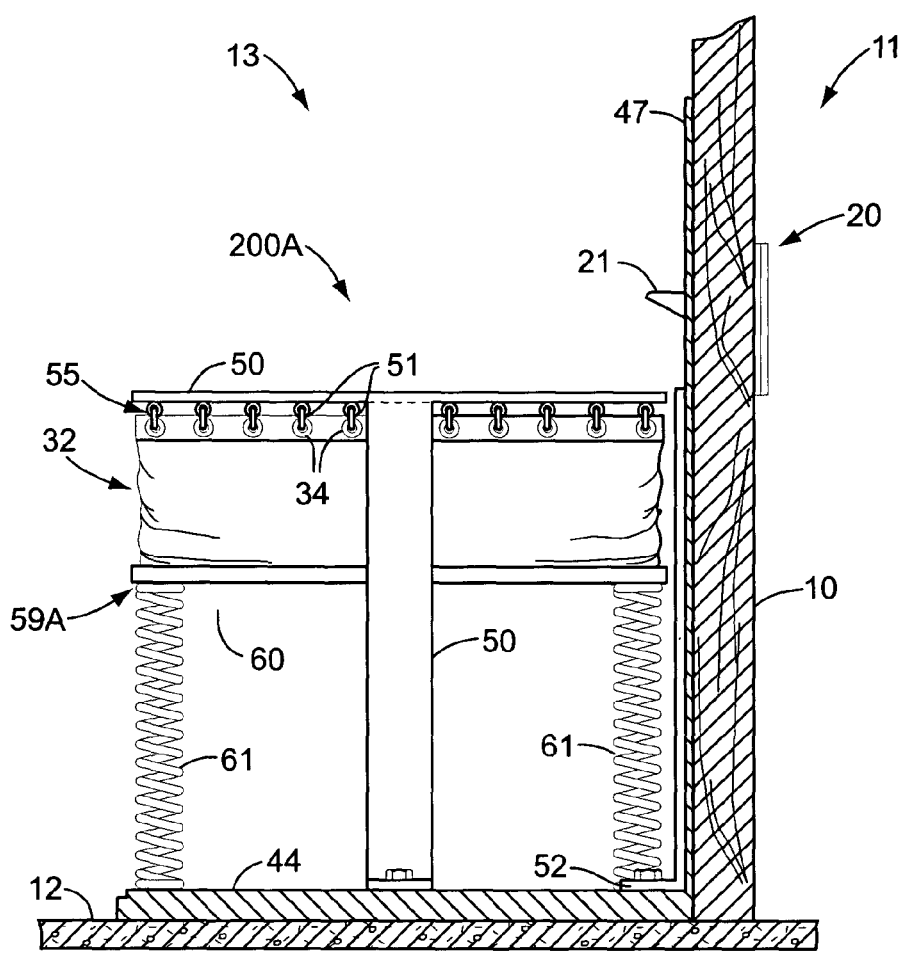
FIG. 4 is a partial side view of the mail collection point-of-use of FIG. 3 as seen on line 4—4 of FIG. 3.

In a second embodiment consistent with the present invention, as illustrated in FIGS. 3 and 4, a mail collection point-of-use 200A comprises the same elements as in point-of-use 200 (FIGS. 1–2), except that it includes a mail receptacle in the form of a sack 32, which is an expandable and collapsible container, as illustrated in FIG. 3, and not rigid, constant-volume container 31 (FIGS. 1–2). Those elements that are in common between points-of-use 200 and 200A will not be described again unless necessary.

Sack 32 comprises a flexible, expandable, and collapsible container. As illustrated, sack 32 may be made of canvas and has grommets 34 spaced along the top edge. Sack 32 may be formed of other flexible material such as polyester, or any material strong enough to support accumulated mail without tearing. Preferably, it should support 40 pounds and 85 pounds tear weight of accumulated mail. An expandable and collapsible container need not be a sack, but could be of other appropriate construction, such as self-supporting plastic or paper container with horizontally, pre-creased walls that will expand and collapse like an accordion or bellow.

Mail collection point-of-use 200A further comprises an upper positioning structure 55 for maintaining the top of sack 32 in an open position and at a fixed distance below opening 27 of mail drop unit 20. As illustrated, upper positioning structure 55 comprises two generally parallel brackets 50, hooks 51, and grommets 34 in sack 32. Each bracket 50 has hooks 51 engaging a plurality of grommets 34 spaced along the top edge of sack 32. Brackets 50 need not be of the shape illustrated, nor mounted on bottom wall 44 of enclosure 40 (FIG. 1), but could be mounted to any wall of enclosure 40 and still perform their function. Brackets 50 could alternatively be replaced by a self-supporting frame that sits on bottom wall 44 of enclosure 40 (FIG. 1). Alternatively, sack 32 need not have grommets 34, but could have rings such as on a. shower curtain to hang over hooks in brackets 50 or frame, or could have loops formed from the same material as the container. Alternatives to hooks and grommets are standard methods of removably securing flexible material to a frame, such as Velcro, interlocking pieces or clips with the material of the container compressed between them, etc. A requirement of these alternatives is that they must support the design weight of a mail receptacle filled with accumulated mail without detaching from the frame, which in this embodiment is around 70 pounds.

Mail collection point-of-use 200A also has a lower positioning structure 59A for establishing the bottom of the mail receptacle at an initial position below the top of the mail receptacle when empty and for lowering the bottom of the mail receptacle as a result of the weight of the accumulated mail. As the weight increases, the bottom of the mail receptacle is lowered a proportional distance. As illustrated in FIGS. 3 and 4, lower positioning structure 59A comprises a rectangular, plywood platform 60 for supporting the bottom of sack 32 and four compressible coiled springs 61. Springs 61 are positioned between platform 60 and bottom wall 44. Each of the four springs 61 supports platform 60 near a different corner and together springs 61 elevate platform 60 and establish the bottom of sack 32 at a position near bottom edge 26 of chute 21, but below the top of sack 32 when empty.

Alternatively, platform 60 could be made of any material sufficiently strong to support the weight of a mail receptacle full of mail without deforming from the localized pressure exerted by springs 61. Platform 60 also may be any shape that supports the bottom of a mail receptacle. Finally, a platform is not needed if the bottom of sack 32 includes a reinforcement member to prevent deformation from the localized pressure produced by springs 61.

If desired, a rectangular plywood base (not shown) may be provided between bottom wall 44 of enclosure 40 and the bottom of springs 61 such that springs 61 are then positioned between platform 60 and the rectangular plywood base. The base may be set on or mounted to bottom wall 44, if desired.

Figure 5:
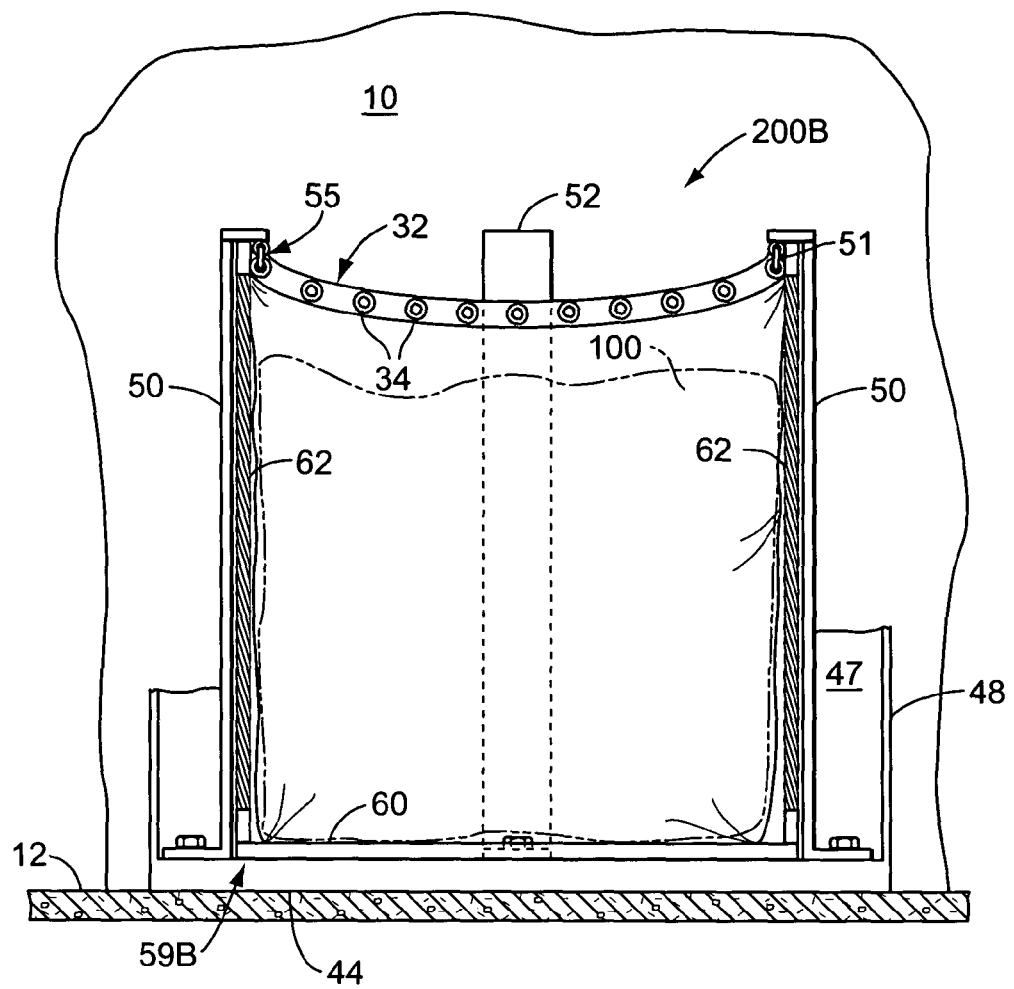
FIG. 5 is a rear view of the sack filled with accumulated mail with four bungee cords attached to the brackets and a platform and stretched a distance proportional to the weight of mail accumulated in the sack.
Figure 6:
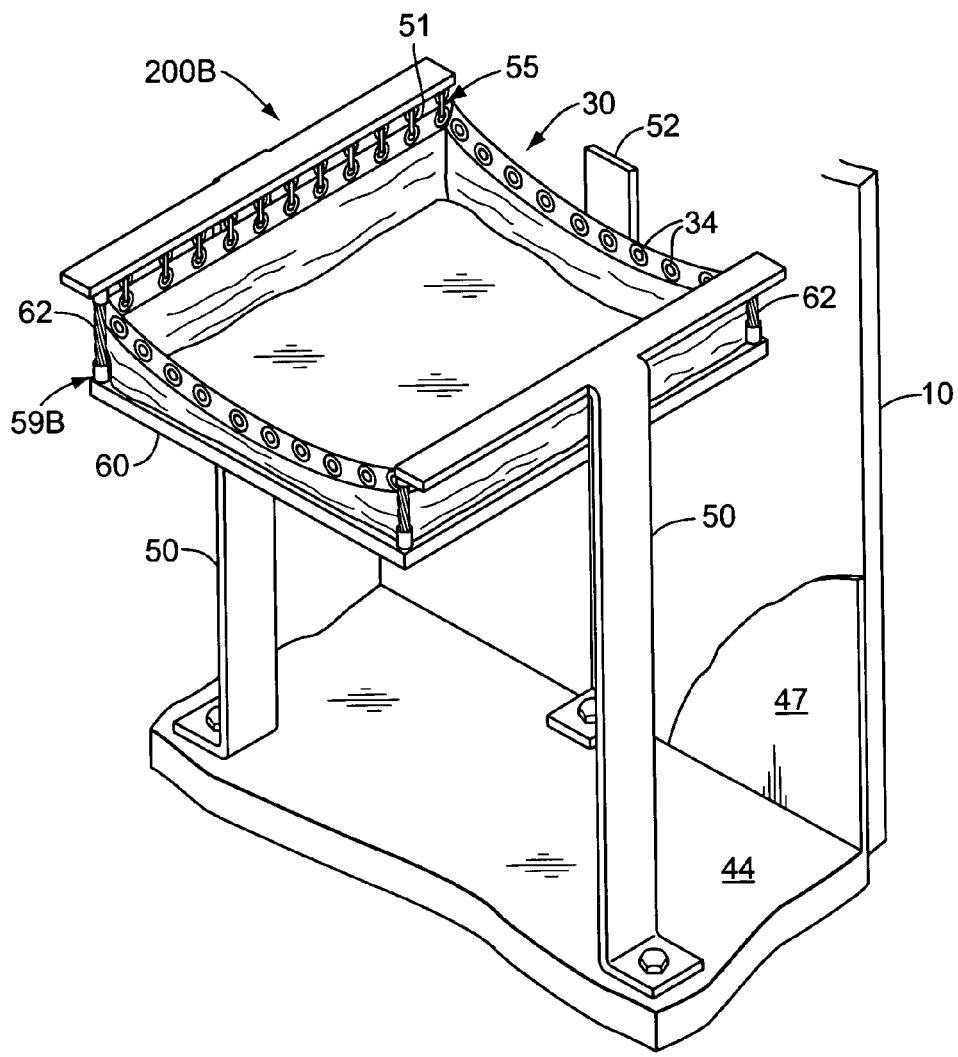
FIG. 6 is a perspective view of the sack of FIG. 5 when the sack is empty and the bungee cords have elevated the platform.
Figure 7:
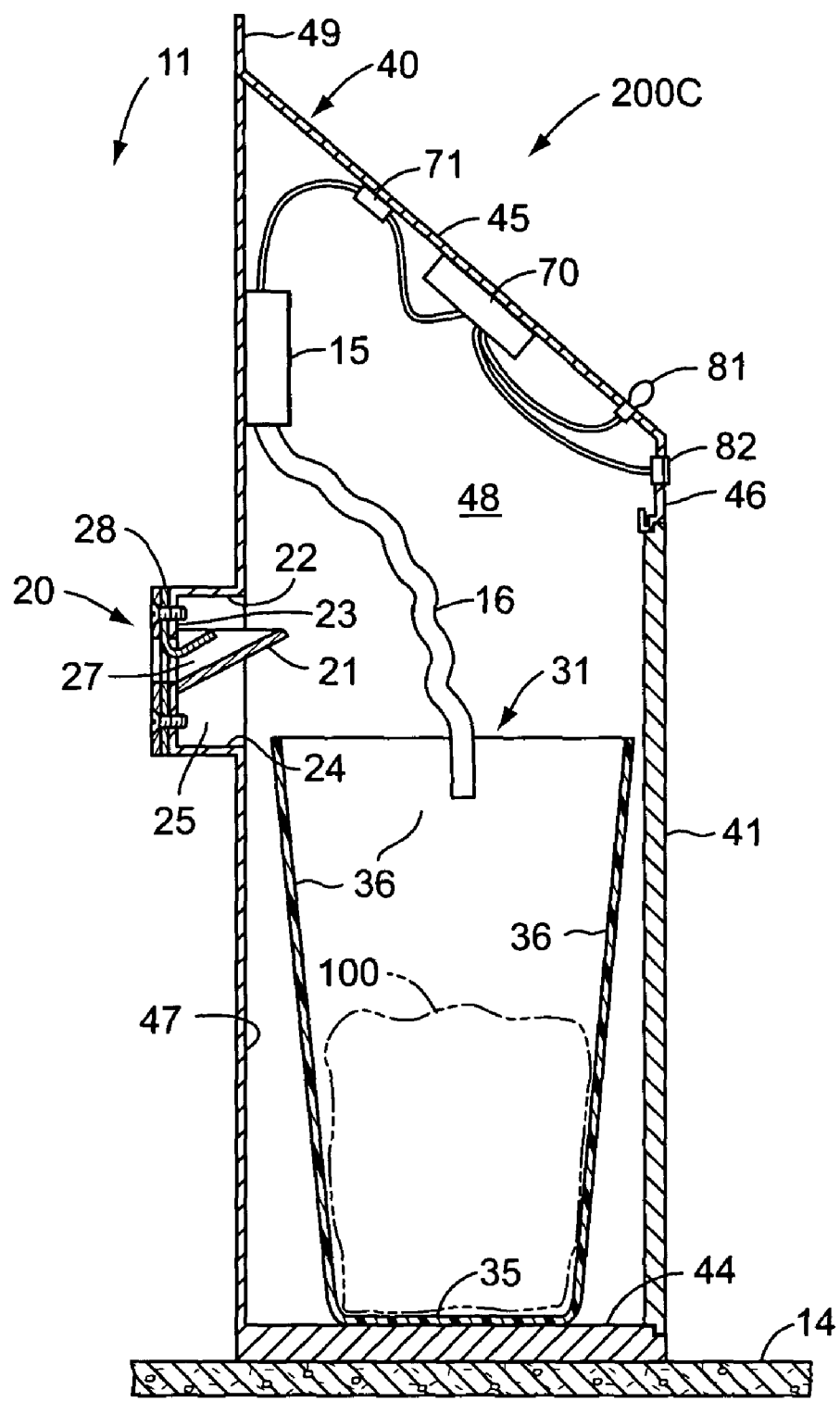
FIG. 7 is a section view of a stand-alone mail collection point-of-use consistent with the invention.

FIGS. 5 and 6 show another mail collection point-of-use 200B, consistent with the invention. Those elements that are the same as mail collection points-of-use 200 and 200A will not be described again unless necessary. In FIGS. 5 and 6, a lower positioning structure 59B has four resilient cords 62, such as bungee cords, and platform 60 and establishes the bottom of sack 32 at an initial position below the top of sack 32 and lower the bottom of sack 32 as a function of the weight of the accumulated mail. Each cord 62 is connected to a corner of platform 60 and the corresponding end of bracket 50 above that corner. As sack 32 accumulates received customer-deposited mail, the weight of accumulated mail 100 stretches cords 62 and lowers platform 60. As the platform 60 lowers, sack 32 expands to accumulate additional, received mail. FIG. 5 illustrates this embodiment when cords 62 are stretched proportionally to the weight of accumulated mail 100 and have lowered the bottom of sack 32 the distance they (bungee cords 62) have stretched.

Embodiments consistent with the invention are not limited to springs or resilient cords for establishing the bottom of the mail receptacle at an upper position below the top of the mail receptacle and for lowering it as a function of the weight of the accumulated mail. Any structure that provides a upward force proportional to weight to the bottom of the mail receptacle, either directly or indirectly, may be used, such as air cylinders or hydraulics in conjunction with appropriate controls.

As shown in FIGS. 5 and 6, platform 60, as it is raised and lowered, is guided by vertical portions of brackets 50 and by an additional vertical guide 52 positioned on the side of platform 60 closest to front wall 47. Vertical guide 52 is mounted to bottom wall 44 of enclosure 40 (FIGS. 1 and 2) and may also provide a boundary for sack 32 as it expands. In certain applications, multiple vertical guides, similar to vertical guide 52, may be added. Vertical guides, like vertical guide 52, do not need to be mounted to bottom wall 44, but can be in a shape for mounting to any wall (44, 45, 46, 47, and 48 as shown in FIGS. 1 and 2) of enclosure 40 (FIGS. 1 and 2). A requirement for any vertical guide is to avoid obstructing the removal of mail receptacle, as sack embodiment 32 or otherwise, from enclosure 40 (FIGS. 1 and 2) through door 41 (FIGS. 1 and 2).

As illustrated in FIGS. 3, 4, and 6, by establishing the bottom of sack 32 when empty to a position closer to bottom edge 26 of chute 21 than bottom wall 44, mail deposited by a customer through opening 27 falls a shorter distance into an empty mail receptacle and lands with a smaller force. This reduced falling distance and landing force reduces the amount of any hazardous material contained in the deposited mail that is dispersed upon landing through openings and porous surfaces in the mail.

In a fourth embodiment consistent with the present invention (not illustrated), a mail collection point-of-use differs from that of the first embodiment in that rigid, constant-volume container 31 is replaced with sack 32 and upper positioning structure 55 as described in mail collection point-of-use 200A.

In a fifth embodiment consistent with the present invention, a mail collection point-of-use 200C differs from that of mail collection point-of-use 200 in that the area outside enclosure 40 (FIGS. 1 and 2) may be completely a generally customer-accessible area 11, without wall 10 separating area 11 from non-customer-accessible work area 13, such that customers may access the area around side walls 48, top wall 45 and back wall 46 of enclosure 40. Flange 49 may be bolted to a floor 14 of customer-accessible area 11. Opening 27 of mail drop unit 20 may be in front wall 47, as top wall 22, bottom wall 24 and side walls 25 no longer need to extend through wall 10 (FIG. 1).

Figure 8:
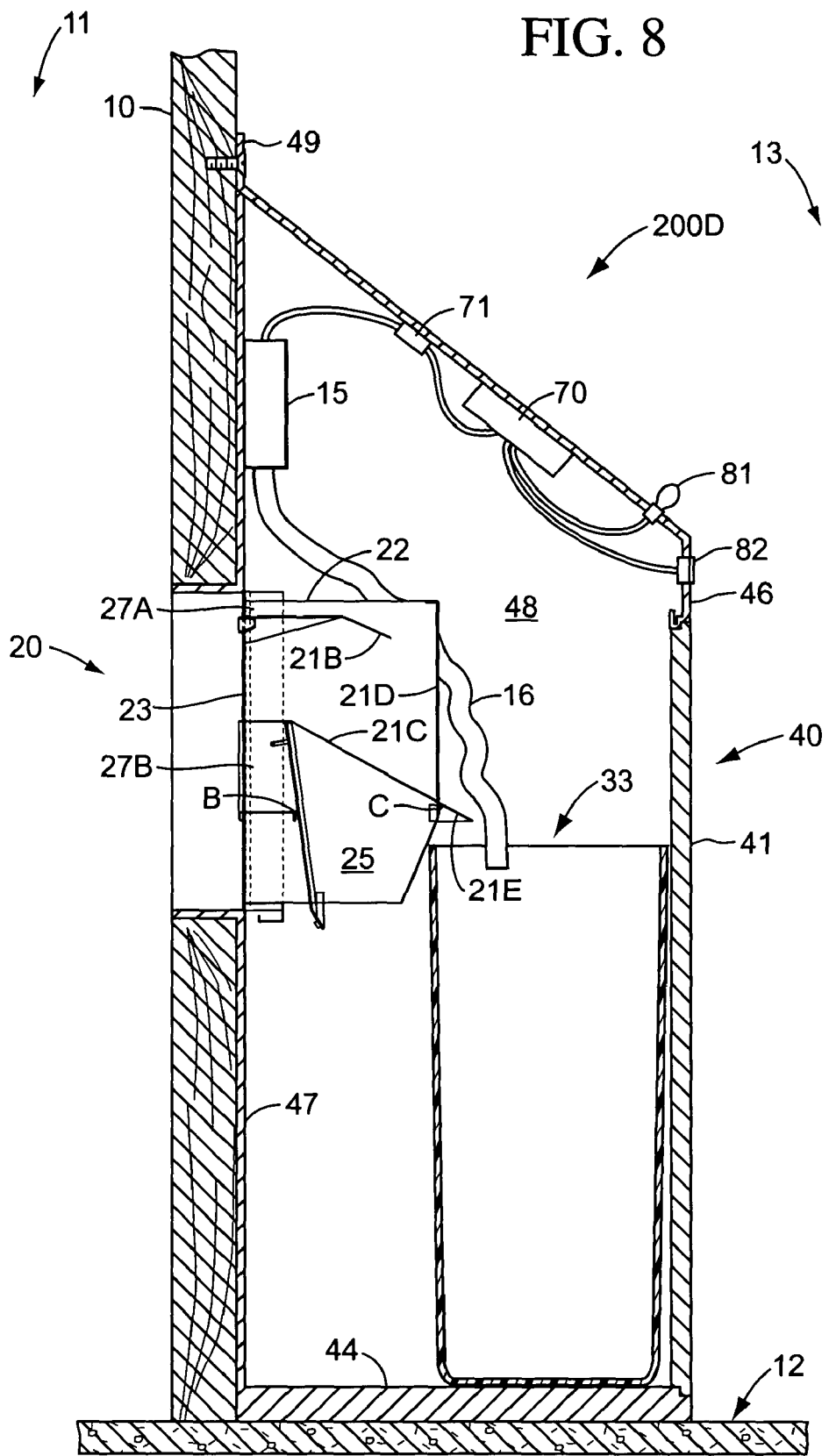
FIG. 8 is a section view of mail collection point-of-use consistent with the invention with a modified 1577 letter drop unit.
Figure 9:
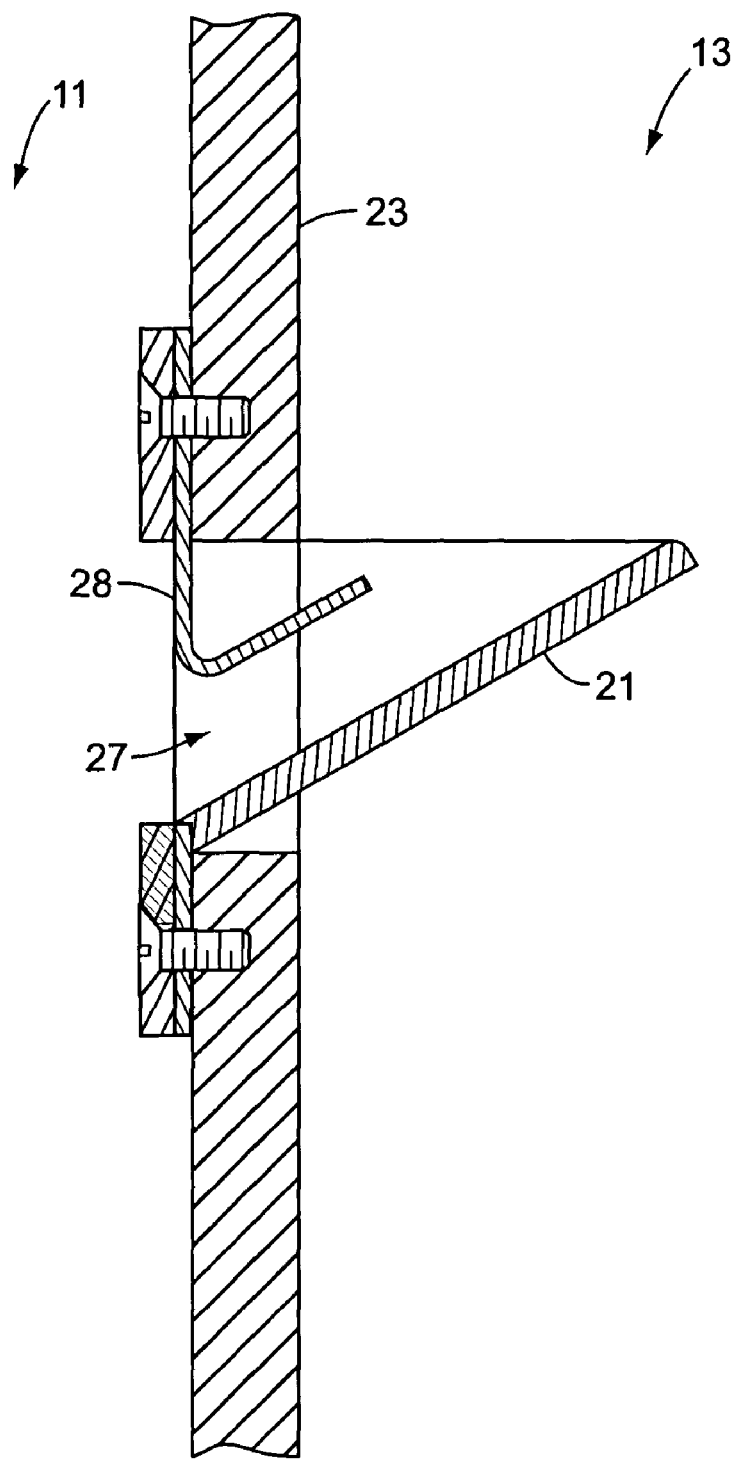
FIG. 9 is a section view of a PS 1814 series face plate drop unit.

Illustrated in FIG. 8 is a sixth embodiment consistent with the present invention: a mail collection point-of-use 200D has a mail drop unit 20 in the form of a modified 1577 letter drop unit and a mail receptacle 33. In all other respects, mail collection point-of-use is the same as mail collection point-of-use 200. Modified 1577 letter drop unit 20 is flush with front wall 47 of enclosure 40, as wall 10 is trimmed to provide access to opening 27A of modified 1577 letter drop unit 20. Letter drop unit 20 may be bolted to brackets, which may be welded to front wall 47. In letter drop unit 20, a hinged door, which covers a second opening 27B, is blocked from rotating about point C and therefore is not used to receive and guide mail. As illustrated in FIG. 9, chute 21B is connected to wall 23 below opening 27A. Chute 21C is connected to wall 23 below chute 21B and is hinged to chute 21D. Chute 21D is magnetically attached to top wall 22, but detaches and rotates about point C when sufficient mail has accumulated to overcome the magnetic force, guiding the mail into container 33. Specific to modifications of a 1577 letter drop unit, chute 21D may be removed altogether and chute 21C extended with piece 21E. FIG. 9 illustrates both modification options. In general a chute could also be a conveyor belt, a tube, a duct, a channel, or a hinged flap drop.

Figure 10:
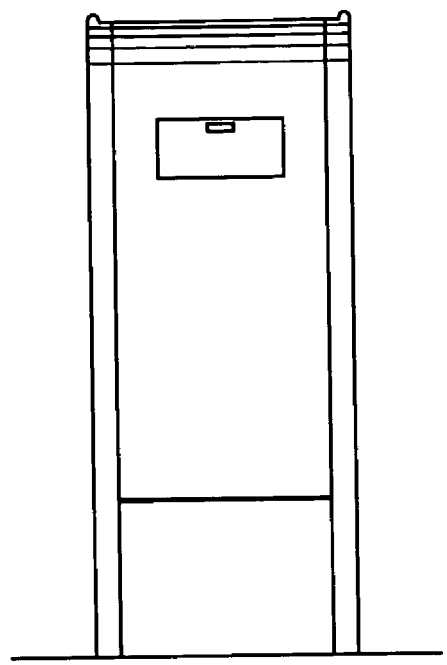
FIG. 10 is a front view of a curbside mail collection point-of-use.
Figure 11:
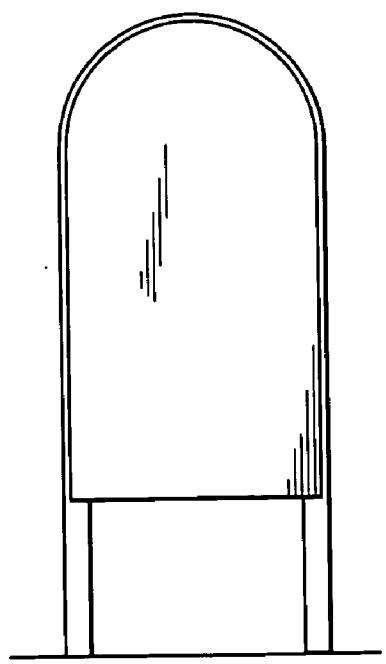
FIG. 11 is a side view of the curbside mail collection point-of-use in FIG. 10.

In a seventh embodiment consistent with the present invention, a mail collection point-of-use, the familiar curbside mailbox, shown in FIGS. 10 and 11, may be retrofitted with any of the aforementioned mail receptacles and any necessary positioning structures, a detector 70, an indicator, fan 15, and switch 71, each sized to fit within the enclosure of the mailbox. Detector 70, indicator 81, and fan 15 may be powered by any appropriate source, including solar power, or the generation of electricity through the manual rotation of the hinged flap door during opening and closing during the deposit of mail into the mail drop.

Other embodiments consistent with the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mail collection point-of-use comprising:
   a mail drop unit comprising an opening for receiving customer-deposited mail;
   an enclosure coupled to the mail drop unit, the enclosure comprising an opening and a door sealing the opening when the door is closed;
   a mail receptacle positioned inside the enclosure, the mail receptacle accumulating received customer-deposited mail, the receptacle and the opening of the enclosure sized to permit removal of the receptacle from the enclosure through the opening;
   a positioning structure establishing a bottom portion of the mail receptacle to a first position below a top portion of the mail receptacle when empty, and lowering the bottom portion of the mail receptacle to a second position as a function of the weight of the received customer-deposited mail;
   a detector positioned inside the enclosure and generating a detection signal upon detection of airborne hazardous material; and
   an indicator positioned outside the enclosure, coupled to the detector, and generating an indication upon receipt of the detection signal.

2. A mail collection point-of-use, at least partially positioned in a first wall separating a customer-accessible area from a non-customer-accessible work area, the mail collection point-of-use comprising:
   a mail drop unit having an opening for receiving customer-deposited mail;
   an enclosure on the non customer-accessible work area side of the wall, the enclosure being sealingly coupled to the mail drop unit and sealed off from the work area, the enclosure comprising an opening and a door sealing the opening when the door is closed;
   a mail receptacle positioned inside the enclosure, the mail receptacle accumulating received customer-deposited mail, the receptacle and the opening of the enclosure sized to permit removal of the receptacle from the enclosure through the opening;
   a positioning structure establishing a bottom portion of the mail receptacle to a first position below a top portion of the mail receptacle when empty, and lowering the bottom portion of the mail receptacle to a second position as a function of the weight of the received customer-deposited mail;
   a detector positioned inside the enclosure and generating a detection signal upon detection of airborne hazardous material; and
   an indicator positioned outside the enclosure, coupled to the detector, and generating an indication upon receipt of the detection.

3. The mail collection point-of-use of claim 2, wherein the enclosure is hermetically coupled to the mail drop unit, hermetically sealed off from the work area, and
   wherein the door hermetically seals the opening of the enclosure when the door is closed.

4. The mail collection point-of-use of claim 2, wherein the mail drop unit comprises top, side, and bottom walls corresponding in size and shape to the surrounding surfaces of the first wall, and means for guiding received mail to the mail receptacle.

5. The mail collection point-of-use of claim 2, wherein the mail drop unit comprises top, side, and bottom walls, and a guide facilitating transport of received mail to the mail receptacle.

6. The mail collection point-of-use of claim 2, wherein the indicator is positioned outside of the enclosure within the non-customer-accessible work area.

7. The mail collection point-of-use of claim 2, wherein the indicator is positioned on an outside surface of the enclosure.

8. The mail collection point-of-use of claim 2 comprising:
   means for increasing the rate at which any airborne hazardous material within the mail receptacle reaches the detector; and
   means coupled to the detector for selectively deactivating the rate-increasing means.

9. The mail collection point-of-use of claim 8, wherein the rate increasing means comprises a duct through which to suck air from the mail receptacle.

10. The mail collection point-of-use of claim 2 comprising:
    a fan sucking and directing air from the mail receptacle;
    means coupled to the detector for selectively deactivating the fan.

11. The mail collection point-of-use of claim 2, wherein the indicator comprises at least one lamp for generating visible light upon receipt of the detection signal.

12. The mail collection point-of-use of claim 2, wherein the indicator comprises an audio emitter generating sound upon receipt of the detection signal.

13. The mail collection point-of-use of claim 2, wherein the enclosure comprises a front, top, back, and two side walls, and the door is positioned on one of the side or back walls.

14. The mail collection point-of-use of claim 2 comprising a first flange extending from the enclosure and abutting the wall for securing the enclosure to the wall.

15. The mail collection point-of-use of claim 2, wherein the mail receptacle comprises a rigid, constant-volume container comprising a bottom and four side walls.

16. The mail collection point-of-use of claim 2 comprising:
means for maintaining the top of the mail receptacle in an open position and at a fixed distance below the opening of the mail drop unit, wherein the mail receptacle comprises an expandable and collapsible container.

17. The mail collection point-of-use of claim 2 comprising:
a second positioning structure maintaining a top portion of the mail receptacle in an open position and at a fixed distance below the opening of the mail drop unit, wherein the mail receptacle comprises an expandable and collapsible container.

18. The mail collection point-of-use of claim 2, wherein the mail receptacle comprises an expandable and collapsible container comprising grommets; and
a plurality of brackets, with hooks coupled to at least one of the brackets and engaging at least one of the grommets.

19. A mail collection point-of-use, at least partially positioned in a first wall separating a customer accessible area from a non-customer-accessible work area, the mail collection point-of-use comprising:
a mail drop unit comprising an opening for receiving customer-deposited mail;
a mail receptacle for accumulating received customer-deposited mail; the mail receptacle comprising an expandable and collapsible container;
a first positioning structure maintaining the top of the mail receptacle in an open position and at a fixed distance below the opening of the mail drop unit;
a second positioning structure establishing the bottom of the mail receptacle to a first position below the top of the mail receptacle when empty and lowering the bottom of the mail receptacle to a second position as a function of the weight of the accumulated mail;
an enclosure on the work area side of the wall, the enclosure being hermetically coupled to the mail drop unit and hermetically sealed off from the work area, the enclosure containing the mail receptacle and comprising an opening sized to permit removal of the mail receptacle and a door hermetically sealing the opening when the door is closed;
a detector positioned inside the enclosure and generating a detection signal upon detection of airborne hazardous material; and
an indicator positioned outside the enclosure, coupled to the detector, and generating an indication upon receipt of the detection.

20. A mail collection point-of-use of claim 19 comprising:
a platform for supporting the bottom of the container; and
at least one vertical guide for providing a boundary for the platform as it moves.

21. A mail collection point-of-use of claim 19 comprising:
a fan for increasing the rate at which any airborne hazardous material reaches the detector; and
a control coupled to the detector for selectively deactivating the fan upon detection of airborne hazardous material.

22. The mail collection point-of-use of claim 19, wherein indicator comprises at least one light bulb for generating visible light upon receipt of the detection signal.

23. The mail collection point-of-use of claim 19, wherein the indicator comprises a buzzer for generating sound upon receipt of the detection signal.

24. The mail collection point-of-use of claim 19, wherein the indicator is positioned on an outside surface of the enclosure.

25. The mail collection point-of-use of claim 19 wherein the container comprises grommets; and
wherein the first positioning structure comprises parallel brackets comprising hooks engaging at least one of the grommets.

26. A mail collection point-of-use, at least partially positioned in a wall separating a customer accessible area from a non-customer-accessible work area, the mail collection point-of-use comprising:
a mail drop unit comprising an opening for receiving customer-deposited mail;
a mail receptacle for accumulating received customer-deposited mail; the mail receptacle comprising an expandable and collapsible container;
a positioning structure maintaining the top of the mail receptacle in an open position and at a fixed distance below the opening of the mail drop unit;
an enclosure on the work area side of the wall, the enclosure being sealingly coupled to the mail drop unit and sealed off from the work area, the enclosure containing the mail receptacle and comprising an opening sized to permit removal of the mail receptacle and a door sealing the opening when the door is closed;
a platform supporting the bottom of the mail receptacle;
a plurality of springs placed between the platform and the bottom of the enclosure, which elevate the platform to a position below the top of the mail receptacle when empty, and which lower the platform proportionally to the weight of mail accumulated in the mail receptacle;
a detector positioned inside the enclosure and generating a detection signal upon detection of airborne hazardous material; and
an indicator positioned outside the enclosure, coupled to the detector, and generating an indication upon receipt of the detection.

27. The mail collection point-of-use of claim 26 comprising:
at least one vertical guide providing a boundary for the mail receptacle as it expands and the platform as it moves.

28. The mail collection point-of-use of claim 26, wherein the platform is rectangular and the plurality of springs comprises four springs positioned at corners of the platform.

29. The mail collection point-of-use of claim 26, wherein the mail receptacle comprises grommets; and
wherein the positioning structure comprises a plurality of brackets comprising hooks engaging at least one of the grommets.

30. The mail collection point-of-use of claim 26, wherein the indicator comprises at least one light bulb for generating visible light upon receipt of the detection signal.

31. The mail collection point-of-use of claim 26, wherein the indicator comprises a buzzer for generating sound upon receipt of the detection signal.

32. The mail collection point-of-use of claim 26, wherein the indicator is positioned on an outside surface of the enclosure.

33. A mail collection point-of-use, at least partially positioned in a wall separating a customer accessible area from a non-customer-accessible work area, the mail collection point-of-use comprising:
  a mail drop unit comprising an opening for receiving customer-deposited mail;
  a mail receptacle for accumulating received customer-deposited mail; the mail receptacle comprising an expandable and collapsible container;
  a positioning structure maintaining the top of the mail receptacle in an open position and at a fixed distance below the opening of the mail drop unit;
  an enclosure on the work area side of the wall, the enclosure being sealingly coupled to the mail drop unit and sealed off from the work area, the enclosure containing the mail receptacle and comprising an opening sized to permit removal of the mail receptacle and a door sealing the opening when the door is closed;
  a platform supporting the bottom of the mail receptacle;
  a plurality of resilient cords, each cord attached at one end to the platform and the other end to the positioning structure, wherein the cords elevate the platform at a first position below the top of the mail receptacle when empty, and which are proportionally stretched by the weight of mail accumulated in the mail receptacle;
  a detector positioned inside the enclosure and generating a detection signal upon detection of airborne hazardous material; and
  an indicator positioned outside the enclosure, coupled to the detector, and generating an indication upon receipt of the detection.

34. The mail collection point-of-use of claim 33 comprising at least one vertical guide providing a boundary for the platform as it moves.

35. The mail collection point-of-use of claim 33, wherein the platform is rectangular and the plurality of cords comprises four cords attached to corners of the platform.

36. The mail collection point-of-use of claim 33, wherein the indicator comprises at least one light bulb for generating visible light when hazardous material is detected.

37. The mail collection point-of-use of claim 33, wherein the indicator comprises a buzzer for generating sound when hazardous material is detected.

38. The mail collection point-of-use of claim 33, wherein indicator is on an outside surface of the enclosure.

39. A mail collection point-of-use, at least partially positioned in a wall separating a customer accessible area from a non-customer-accessible work area, the mail collection point-of-use comprising:
  a mail drop unit comprising an opening for receiving customer-deposited mail; a mail receptacle for accumulating received customer-deposited mail; the mail receptacle comprising an expandable and collapsible container;
  means for maintaining the top of the mail receptacle in an open position and at a fixed distance below the opening of the mail drop unit;
  means for establishing the bottom of the mail receptacle at a first position below the top of the mail receptacle when empty and lowering the bottom of the mail receptacle as a function of the weight of the accumulated mail;
  an enclosure on the work area side of the wall, the enclosure being sealingly coupled to the mail drop unit and sealed off from the work area, the enclosure containing the mail receptacle and comprising an opening sized to permit removal of the mail receptacle and a door hermetically sealing the opening when the door is closed;
  a detector positioned inside the enclosure and generating a detection signal upon detection of airborne hazardous material; and
  an indicator positioned outside the enclosure, coupled to the detector, and generating an indication upon receipt of the detection signal.

40. A mail collection point-of-use, at least partially positioned in a wall separating a customer-accessible area from a non-customer-accessible work area, the mail collection point-of-use comprising:
  a mail drop unit comprising an opening for receiving customer-deposited mail; a mail receptacle for accumulating received customer-deposited mail the mail receptacle comprising a sack;
  means for maintaining the top of the mail receptacle in an open position and at a fixed distance below the opening of the mail drop unit;
  a platform, which supports the bottom of the sack;
  means for establishing the bottom of the sack at a first position below the top of the sack when empty and lowering the bottom of the sack as a function of the weight of mail accumulated in the sack; and
  at least one vertical guide for providing a boundary for the sack as it expands and the platform as it moves.

41. The mail collection point-of-use of claim 40, wherein:
  the sack comprises grommets, and
  the maintaining means comprises a plurality brackets comprising hooks engaging the grommets.

42. The mail collection point-of-use of claim 40, wherein:
  the establishing means comprises a plurality of springs positioned between the platform and the floor of the work area.

43. The mail collection point-of-use of claim 42, wherein:
  the platform is rectangular and the plurality of springs comprises four springs positioned near corners of the platform.

44. The mail collection point-of-use of claim 40, wherein:
  the establishing means comprises a plurality of resilient cords, each cord attached at one end to the platform and at the other end to a corresponding one of the brackets.

45. The mail collection point-of-use of claim 44, wherein:
  the platform is rectangular and the plurality of cords comprises four cords attached to corners of the platform.

46. The mail collection point-of-use of claim 40, wherein:
  the sack comprises grommets;
  the maintaining means comprises a plurality of brackets comprising hooks engaging at least one of the grommets; and
  wherein the establishing means comprises plurality of springs positioned between the platform and the floor of the work area.

47. The mail collection point-of-use of claim 40 wherein:
  the sack comprises grommets;

the maintaining means comprises a plurality of brackets comprising hooks engaging at least one of the grommets; and the establishing means comprises a plurality of resilient cords, each cord attached at one end to the platform and at the other end to a corresponding one of the brackets.

48. A method of preventing detected hazardous materials within a mail collection point-of-use from contaminating components of subsequent mail delivery system processes, the method comprising:

receiving customer-deposited mail through an opening in a mail drop unit;

reducing the distance received customer-deposited mail falls before landing in an empty mail receptacle;

accumulating received mail in a mail receptacle contained in an enclosure;

examining air within the enclosure for airborne hazardous material;

generating a detection signal if hazardous material is detected; and indicating the detection of hazardous material.

49. The method of claim 48 comprising isolating accumulated mail and the surrounding air in the enclosure from a non-customer-accessible work area containing the enclosure.

50. The method of claim 48 comprising facilitating airflow within the enclosure until a detection signal is generated.

51. The method of claim 48, wherein the method of indicating the detection of hazardous material comprises illuminating a visible light source or generating an audible sound.

* * * * *

UNITED STATES PATENT AND TRADEMARK OFFICE
CERTIFICATE OF CORRECTION

PATENT NO. : 7,095,323 B2
APPLICATION NO. : 10/632466
DATED : August 22, 2006
INVENTOR(S) : Harry Darty It is certified that error appears in the above-identified patent and that said Letters Patent is hereby corrected as shown below:

In claim 2, column 8, line 7, "non customer-accessible" should read --non-customer-accessible--.

In claim 10, column 8, line 62, after "receptacle;" insert --and--.

In claim 19, column 9, line 34, "customer accessible" should read --customer-accessible--.

In claim 19, column 9, line 40, "mail;" should read --mail,--.

In claim 25, column 10, line 16, "claim 19 wherein" should read --claim 19, wherein--.

In claim 26, column 10, line 22, "customer accessible" should read --customer-accessible--.

In claim 26, column 10, line 28, "mail;" should read --mail,--.

In claim 33, column 11, line 9, "customer accessible" should read --customer-accessible--.

In claim 33, column 11, line 15, "mail;" should read --mail,--.

In claim 38, column 11, lines 53-54, "wherein indicator" should read --wherein the indicator--.

In claim 39, column 11, Line 56, "customer accessible" should read --customer-accessible--.

In claim 39, column 11, line 62, "mail;" should read --mail,--.

In claim 40, column 12, line 25, "mail the" should read --mail, the--.

In claim 41, column 12, line 39, "plurality brackets" should read --plurality of brackets--.

UNITED STATES PATENT AND TRADEMARK OFFICE
CERTIFICATE OF CORRECTION

PATENT NO. : 7,095,323 B2
APPLICATION NO. : 10/632466
DATED : August 22, 2006
INVENTOR(S) : Harry Darty It is certified that error appears in the above-identified patent and that said Letters Patent is hereby corrected as shown below:

In claim 46, column 12, line 63, "comprises plurality" should read --comprises a plurality--.

Signed and Sealed this

Twenty-first Day of November, 2006

JON W. DUDAS
*Director of the United States Patent and Trademark Office*